United States Patent [19]

Merger et al.

[11] 4,359,584
[45] Nov. 16, 1982

[54] PREPARATION OF P-SUBSTITUTED, AROMATIC AMINES

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 185,401

[22] Filed: Sep. 8, 1980

[30] Foreign Application Priority Data

Sep. 22, 1979 [DE] Fed. Rep. of Germany ....... 2938764

[51] Int. Cl.$^3$ ............................................. C07C 85/02
[52] U.S. Cl. .................................... 564/393; 564/409; 564/414
[58] Field of Search ........................ 564/393, 409, 414

[56] References Cited

U.S. PATENT DOCUMENTS

| | | | |
|---|---|---|---|
| 2,092,973 | 9/1937 | Herstein | 564/414 |
| 2,115,884 | 3/1938 | Schöllkopf | 564/374 X |
| 2,159,370 | 5/1939 | Dreisbach | 564/407 |
| 2,507,755 | 5/1950 | Boyd | 564/309 |
| 3,123,644 | 3/1964 | Olin | 564/409 |
| 3,222,401 | 12/1965 | Schmerling | 564/409 |
| 3,230,257 | 1/1966 | Schmerling | 564/408 |
| 3,418,371 | 12/1968 | Krimm et al. | 564/330 X |
| 3,761,520 | 9/1973 | Napolitano | 564/409 |
| 4,177,211 | 12/1979 | Sun | 564/330 |

FOREIGN PATENT DOCUMENTS

| | | |
|---|---|---|
| 757983 | of 0000 | Belgium . |
| 757983 | of 0000 | France . |
| 1048277 | 1/1959 | Fed. Rep. of Germany . |
| 1051271 | 2/1959 | Fed. Rep. of Germany . |
| 1056138 | 4/1959 | Fed. Rep. of Germany . |
| 4849925 | of 0000 | Japan . |
| 846226 | 8/1960 | United Kingdom . |

OTHER PUBLICATIONS

Houben–Weyl, "Methoden der Organischen Chemie", vol. 11, No. 1, pp. 248–249 (1957).
Smith, Open–Chain Nitrogen Compounds", vol. 1, pp. 259–263 (1965).
J. Org. Chem., vol. 22, (1957), "Ortho Alkylation of Aniline with Styrene", p. 1752.
Neuere Methoden der Präparativen Organischen Chemie II, 7. Alkylierung Aromatischer Amine, pp. 124–131.

*Primary Examiner*—Robert V. Hines
*Attorney, Agent, or Firm*—Keil & Witherspoon

[57] ABSTRACT p-Substituted aromatic amines are prepared by reacting a p-substituted, aromatic carbamic acid ester with an aromatic amine in the presence of an aliphatic or cycloaliphatic alcohol. The aromatic amines obtainable by the process according to the invention are antiseptics and valuable starting materials for the preparation of dyes, resins, finishes, plastics, pesticides and drugs.

6 Claims, No Drawings

PREPARATION OF P-SUBSTITUTED, AROMATIC AMINES

The present invention relates to a novel process for the preparation of p-substituted, aromatic amines by reacting a p-substituted, aromatic carbamic acid ester with an aromatic amine in the presence of an aliphatic or cycloaliphatic alcohol.

U.S. Pat. No. 2,159,370 discloses the preparation of nuclear-alkylated anilines by ammonolysis of alkylated halobenzenes at 150°–250° C. An isomer mixture of the corresponding alkyl-substituted anilines, especially containing m-alkylaniline, is obtained.

British Patent 846,226 describes the alkylation of anilines with isobutylene at 150°–300° C. in the presence of an activated bleaching earth of the montmorillonite type. Depending on the reaction temperature, isomer mixtures or predominantly p-alkylated anilines are formed. German Published Application DAS No. 1,051,271 describes the formation of ortho-alkylated anilines, accompanied by slight N-alkylation, by reaction of an aromatic amine with an olefin at 150°–250° C. in the presence of a Friedel-Crafts catalyst, sulfuric acid, phosphoric acid or a bleaching earth (montmorillonite). U.S. Pat. No. 2,115,884 discloses the preparation of N-alkylated, aromatic amines by reacting the corresponding amine with an olefin in the presence of an acid-activated bleaching earth, alumina, kaolin or another silicate. U.S. Pat. No. 3,230,257 describes the nuclear alkylation and N-alkylation of the hydrogen halide salts of aromatic amines by reaction with an olefin at 200°–400° C. German Published Applications DAS No. 1,048,277 and DAS No. 1,056,138 also describe the formation of ortho-nuclearalkylated anilines by reaction of an olefin with an aniline in the presence of a Friedel-Crafts catalyst or of a bleaching earth and, simultaneously, of aluminum or an aluminum compound of an aromatic amine, or, simultaneously, an alkali metal or alkaline earth metal or an anilide of these, at 250°–350° C. and 100–200 atmospheres.

The disadvantage of the above processes is that they must be carried out at relatively high temperatures. Under these conditions, many olefins produce side-reactions, for example oligomerization or rearrangements. Furthermore, in the case of volatile materials a high reaction temperature entails the use of high pressures and hence of complicated apparatus. Furthermore, the reactions are non-selective. In addition to the ortho-, meta- and para-isomers, N-alkylated amines are formed, sometimes in considerable amount.

U.S. Pat. No. 3,123,644 describes the preparation of para-alkylated aromatic amines by reacting a polyalkylated, aromatic amine with a para-unsubstituted aromatic amine at 150°–350° C. under pressure in the presence of an aluminum silicate. A disadvantage is the expensive preparation of the polyalkylated aromatic amine. Furthermore, the conversion is merely 61 percent, based on polyalkylated aromatic amine.

U.S. Pat. No. 2,507,755 describes the preparation of p-alkylanilines by reacting aniline with an alkylphenol at 100°–250° C. and 30–140 bar in the presence of $ZnCl_2$ alone or of a combination of $ZnCl_2$ with an aniline hydrohalide. A disadvantage of this process is the expensive working-up required, involving hydrochloric acid and bases and polluting the environment. The conversion is only 11 percent, based on aniline, and the selectivity is 63 percent.

We have found that p-substituted, aromatic amines of the formula

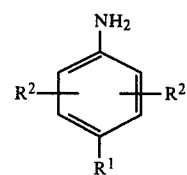

where the individual radicals $R^1$ and $R^2$ may be identical or different and each is an araliphatic or aliphatic radical, $R^1$ may also be a monocyclic or bicyclic cycloaliphatic radical and each $R^2$ may also be an aliphatic-aromatic or aromatic radical, hydrogen or halogen, are obtained in an advantageous manner when a p-substituted, aromatic carbamic acid ester of the formula

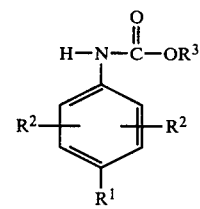

where $R^1$ and $R^2$ have the above meanings and $R^3$ is an aliphatic radical, is reacted with an aromatic amine of the formula

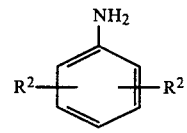

where $R^2$ has the above meanings, in the presence of an aliphatic alcohol of the formula $$R^4\text{—OH} \qquad \text{IV}$$

where $R^4$ is an aliphatic or cycloaliphatic radical.

Where aniline and ethyl p-tert.-butylcarbamate are used, the reaction may be represented by the following equation:

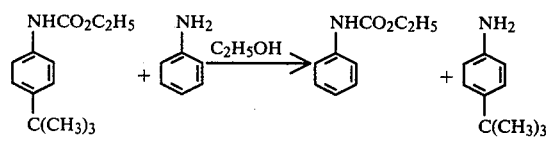

Compared to the conventional processes, the process according to the invention surprisingly gives a large number of p-substituted aromatic amines more simply and more economically, in better yield, higher space-time yield and greater purity. Furthermore, in contrast to the conventional processes for the cleavage of carbamic acid esters, the novel process does not result in the loss of the alkoxycarbonyl group, nor does it require acids or substantial amounts of bases, which on working up pollute the effluent. Thus, the p-unsubstituted carbamic acid ester formed as a by-product can be reacted afresh with an olefin to give the starting material II, which can thus be re-used for the reaction according to the invention. All these advantageous results are surprising in view of the prior art, since it is known from Houben-Weyl, Methoden der Organischen Chemie, volume 11/1, pages 948-949, that carbamic acid esters can be cleaved at elevated temperatures both in an acid medium, preferably by means of strong hydrochloric acid or sulfuric acid, and in an alkaline medium, preferably by means of an alkali metal hydroxide in alcoholic solution. Furthermore, the amines from which the carbamic acid esters are derived can be liberated by distillation with calcium hydroxide or by heating with water at 200°-250° C. under pressure (Houben-Weyl, loc. cit., page 949). Since it is known that the reaction of carbamic acid esters with amines at above 140° C. is used for the preparation of ureas (Houben-Weyl, loc. cit., volume 8, page 161), it is surprising that the reaction of carbamic acid esters with amines in the presence of alcohols does not lead to substantial amounts of ureas.

The aniline III can be reacted with the p-substituted, aromatic carbamic acid ester II in stoichiometric amount, in excess, or in less than stoichiometric amount; the preferred ratio is from 4 to 20, especially from 8 to 16, moles of starting material III per mole of carbamic acid ester II. The alcohol IV is preferably used in an amount of from 1 to 20, advantageously from 1 to 15, especially from 3 to 10, moles of alcohol IV per mole of carbamic acid ester II. Preferred aromatic carbamic acid esters II, anilines III and alcohols IV and, accordingly, preferred aromatic amines I are those where, in the respective formulae, the individual radicals $R^1$, $R^2$, $R^3$ and $R^4$ are identical or different and each is alkyl of 1 to 12, especially of 1 to 6, carbon atoms, $R^1$ may also be cycloalkyl of 5 to 8 carbon atoms, norbornyl or aralkyl of 7 to 12 carbon atoms and in particular alkyl of 3 to 6 carbon atoms, $R^2$ may also be hydrogen, bromine, chlorine, alkylaryl or aralkyl of 7 to 12 carbon atoms, or phenyl, and $R^4$ may also be cycloalkyl of 5 to 8 carbon atoms. The above radicals may additionally be substituted by groups which are inert under the reaction conditions, for example alkyl or alkoxy of 1 to 4 carbon atoms, or (as far as substituents of the phenyl radical are concerned) chlorine or bromine. In a preferred embodiment, the starting materials II, III and IV used are such that the individual radicals $R^2$ in starting material III have the same meaning as the corresponding radicals $R^2$ in starting material II, and $R^4$ has the same meaning as $R^3$, ie. the carbamic acid ester II is derived from the amine III and the alcohol IV.

Examples of suitable aromatic amines III are unsubstituted aniline, and aniline monosubstituted in the 2-, 3-, 5- or 6-position or disubstituted in the 2- and 3-, 2- and 5- or 2- and 6-position by chlorine, bromine, methyl, ethyl, propyl, isopropyl, butyl or isobutyl, the substituents, in the case of the disubstituted products, being identical or different; preferred aromatic amines are aniline, o-toluidine, m-toluidine, o-chloroaniline, m-chloroaniline, o-ethylaniline, o-propylaniline, 2-chloro-6-methylaniline, 5-chloro-2-methylaniline and 2,5-dimethylaniline.

Examples of aromatic carbamic acid esters II suitable for the reaction are the methylcarbamates derived from the anilines III mentioned as examples in the preceding paragraph, the phenyl nucleus being substituted by tert.-butyl in the p-position relative to the carbamido group; the corresponding ethyl, propyl, iospropyl, butyl, sec.-butyl, isobutyl, cyclohexyl and cyclopentyl carbamates; and corresponding carbamates substituted in the p-position by ethyl, methyl, propyl, isopropyl, butyl, sec.-butyl, pentyl, isopentyl, isoheptyl, benzyl, α-phenylethyl, β-phenylethyl, cumyl, norbornyl, cyclohexyl or cyclopentyl; preferred esters are methyl, ethyl, propyl and butyl p-tert.-butylphenyl-, 4-tert.-butyl-2-methylphenyl-, 4-tert.-butyl-2-chloro-phenyl-, 4-tert.-butyl-5-chloro-2-methylphenyl-, 4-tert.-amylphenyl-, p-cyclohexylphenyl-, p-cyclopentylphenyl-, 4-cyclopentyl-2-methylphenyl-, 4-(α-phenylethyl)-phenyl-, 2-chloro-4-(α-phenylethyl)-phenyl-, 4-cumylphenyl-, 4-benzylphenyl-, 4-norbornylphenyl- and 2-chloro-4-norbornylphenyl-carbamate.

Examples of alcohols IV suitable for the reaction are those from which the carbamic acid esters II mentioned as examples in the preceding paragraph are derived, in particular methanol, ethanol, propanol, butanol and isopropanol.

The reaction is in general carried out at from 100° to 260° C., preferably from 130° to 250° C., especially from 150° to 200° C., under reduced pressure, superatmospheric pressure or atmospheric pressure, continuously or batchwise. Advantageously, an additional solvent is not used; at times, however, a solvent which is inert under the reaction conditions may be employed, for example to lower the viscosity of the reaction mixture. Examples of suitable solvents are aliphatic and cycloaliphatic hydrocarbons, eg. heptane, nonane, gasoline fractions within a boiling range of from 70° to 190° C., cyclohexane, methylcyclohexane, naphtha, halohydrocarbons, especially chlorohydrocarbons, eg. tetrachloroethylene, carbon tetrachloride and chlorobenzene, aromatic hydrocarbons, eg. benzene, toluene and xylenes, tetrahydrofuran, dioxane, and mixtures of these. Advantageously, the solvent is used in an amount of from 10 to 1,000 percent by weight, preferably from 50 to 200 percent by weight, based on starting material II.

In an advantageous embodiment, the reaction is carried out in the presence of a basic compound, advantageously used in an amount of from 0.001 to 0.2, preferably from 0.005 to 0.1, equivalent per mole of starting material II. Preferred basic compounds are alkaline earth metal compounds, alkali metal compounds, tertiary amines and mixtures of these. Suitable tertiary amines may be aliphatic, cycloaliphatic, araliphatic, aromatic or heterocyclic. Specific examples of suitable basic compounds are potassium hydroxide, sodium hydroxide, potassium carbonate, sodium carbonate, lithium hydroxide, lithium carbonate, calcium hydroxide, calcium oxide, barium oxide, magnesium hydroxide, magnesium oxide, barium hydroxide, sodium methylate, sodium ethylate, sodium propylate, sodium isopropylate, sodium butylate, potassium methylate, potassium ethylate, triethylamine, tripropylamine, triisopropylamine, tributylamine, n, n-dimethylaniline, 1,4-diazabicyclo-(2,2,2)-octane, 1,5-diazabicyclo-(4,3,0)-non-5-ene, N-methylpiperidine, N-ethylpiperidine and pyridine. Sodium methylate, sodium ethylate, sodium hydroxide and potassium hydroxide are preferred.

The reaction may be carried out as follows: a mixture of starting materials II and III, alcohol IV and—where appropriate—catalyst and/or solvent is kept at the reaction temperature for from 1 to 10 hours. The end product I is then isolated from the reaction mixture in a conventional manner, for example by fractional distillation.

The aromatic amines I obtainable by the process according to the invention are antiseptics and valuable starting materials for the preparation of dyes, resins, finishes, plastics, pesticides and drugs. They, and their secondary products, may be used as antioxidants in the production of synthetic rubber, and as starting materials for the preparation of scents and active materials in pharmaceuticals and crop protection agents. Regarding the use of the compounds, reference may be made to U.S. Pat. No. 3,123,644, British Pat. No. 846,226, Japanese Pat. No. 4,849,925, Belgian Pat. No. 757,983, the publications cited earlier and Ullmanns Encyklopädie der technischen Chemie (3rd edition), volume 5, pages 300–357.

In the Examples which follow, parts are by weight and bear the same relation to parts by volume as that of the kilogram to the liter.

EXAMPLE 1

A mixture of 110 parts of ethyl N-(4-tert.-butylphenyl)-carbamate, 370 parts of aniline and 700 parts of ethanol is heated to 180° C. in an autoclave and kept at this temperature for 6 hours. The mixture is then subjected to fractional distillation under reduced pressure. 60 parts (80% of theory) of 4-tert.-butylaniline, of boiling point 93°–94° C./4 mbar, are obtained.

EXAMPLE 2

A mixture of 110 parts of methyl N-(4-tert.-pentylphenyl)-carbamate, 400 parts of aniline, 400 parts of methanol and 0.2 part of sodium methylate is heated to 200° C. in an autoclave and kept at this temperature for 4 hours. The mixture is then subjected to fractional distillation under reduced pressure. 67 parts (83% of theory) of 4-tert.-pentylaniline, of boiling point 140°–142° C./16 mbar, are obtained.

We claim:

1. A process for the preparation of p-substituted, aromatic amines of the formula

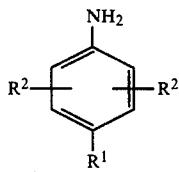

where the individual radical $R^1$ and $R^2$ may be identical or different and each is an araliphatic or aliphatic radical, $R^1$ may also be a monocyclic or bicyclic cycloaliphatic radical and each $R^2$ may also be an aliphatic-aromatic or aromatic radical, hydrogen or halogen, wherein a p-substituted, aromatic carbamic acid ester of the formula

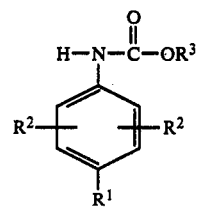

where $R^1$ and $R^2$ have the above meanings and $R^3$ is an aliphatic radical, is reacted with an aromatic amine of the formula

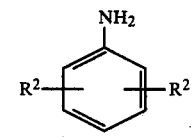

where $R^2$ has the above meanings, in the presence of an aliphatic alcohol of the formula

where $R^4$ is an aliphatic or cycloaliphatic radical.

2. A process as claimed in claim 1, wherein the reaction is carried out with from 4 to 20 moles of starting material III per mole of carbamic acid ester II.

3. A process as claimed in claim 1, wherein the reaction is carried out with from 1 to 20 moles of alcohol IV per mole of carbamic acid ester II.

4. A process as claimed in claim 1, wherein the reaction is carried out at from 100° to 260° C.

5. A process as claimed in claim 1, wherein the reaction is carried out at from 130° to 250° C.

6. A process as claimed in claim 1, wherein the reaction is carried out in the presence of from 0.001 to 0.2 equivalent of a basic compound per mole of starting material II.

* * * * *

UNITED STATES PATENT AND TRADEMARK OFFICE
CERTIFICATE OF CORRECTION

PATENT NO. : 4,359,584
DATED : November 16, 1982
INVENTOR(S) : Franz MERGER and Gerhard NESTLER It is certified that error appears in the above-identified patent and that said Letters Patent is hereby corrected as shown below:

On the title page
[30]  Foreign Application Priority Data should read:

-[30]  Foreign Application Priority Data

Sep. 22, 1979 [DE]   Fed. Rep. of Germany ...... 2938376--

Signed and Sealed this

Nineteenth Day of July 1983

[SEAL]

Attest:

GERALD J. MOSSINGHOFF

Attesting Officer   Commissioner of Patents and Trademarks